(12) United States Patent
Reynard

(10) Patent No.: US 6,520,955 B2
(45) Date of Patent: Feb. 18, 2003

(54) PHACOPHOTOLYSIS METHOD AND APPARATUS

(76) Inventor: Michael Reynard, 1301 - 20th St., #260, Santa Monica, CA (US) 90404

( * ) Notice: Subject to any disclaimer, the term of this patent is extended or adjusted under 35 U.S.C. 154(b) by 104 days.

(21) Appl. No.: 09/749,507

(22) Filed: Dec. 28, 2000

(65) Prior Publication Data

US 2002/0123744 A1 Sep. 5, 2002

(51) Int. Cl.$^7$ ............................................. A61B 18/18
(52) U.S. Cl. ................... 606/4; 606/6; 604/43
(58) Field of Search ................ 606/4, 5, 6; 604/43

(56) References Cited

U.S. PATENT DOCUMENTS 5,957,928 A * 9/1999 Kirwan, Jr. ................. 604/43

* cited by examiner

Primary Examiner—Edward K. Look
Assistant Examiner—Dwayne J. White
(74) Attorney, Agent, or Firm—Albert O. Cota

(57) ABSTRACT

A process and apparatus for removing cataractous lens tissue (22) in a human or animal eye and substitution of the lens with replacement material (48) utilizing an apparatus in the form of a surgical instrument (42). The process contains the steps of injecting a therapeutic photosensitive agent (20) into the lens tissue, allowing a predetermined amount of time to elapse, exposing the photosensitive substance to a source of light energy at a predetermined period of time and wavelength causing the lens to microfracture and liquefy. Following this procedure the liquefied lens tissue is evacuated with the surgical instrument, and a lens replacement material is injected into the lens capsule (28) through the surgical instrument to reconstitute the intralenticular space and serve as a refracting medium. The dual cannula surgical instrument consists of a hollow cylindrical body (52) with a parallel shank (58) and a tapered section (60) on one end. An outer hollow needle (62) attached to the tapered section and an inner hollow needle (64) is axially disposed within the body and outer needle with both needles terminating at the same end. The opposite end of the body is in communication with an aspiration and infusion apparatus for withdrawing decomposed cataractous lens tissue under negative pressure and for supplying irrigation fluids.

39 Claims, 5 Drawing Sheets

PHACOPHOTOLYSIS METHOD AND APPARATUS

TECHNICAL FIELD

The present invention relates to photodynamic therapy for treatment of ocular disease in general. More specifically to the use of refractive polymers in the treatment of cataracts.

BACKGROUND ART

Previously, the primary approach to cataract removal has focused primarily on the use of tissue ablation employing ultrasonic or laser energy. Cataracts removed by this extra-capsular method require extraction of the anterior capsule and lens substance but leave intact the posterior capsule of the lens. Extracapsular surgical techniques are usually performed by technologies that rely on high-impact energy pulses to shatter the lens into fractions that must be constantly degraded further before they may be removed by aspiration. The process of lens fractionalization and removal demands a high level of skill which is tedious and time consuming.

Lens proteins and their constituent amino acids have been studied to determine their behavior in response to radiation. Although most of the amino acids of which proteins are comprised do not absorb ultraviolet light (of a wavelength greater than 220 nm) tryptophan, and to a lessor phenylalanine and tyrosine, are known to absorb significant amounts of ultraviolet light and as a result to be susceptible to structural degradation a process herein referred as "phacophotolysis". Tryptophan photodegradation may, for example, be induced through irradiation at wavelengths between 240–310 nm, and the efficiency of photodegradation is influenced by a number of factors including pH, temperature and encapsulation of photodynamic components in liposomes. Liposomal preparations are particularly useful where the photosensitizing agent is a green porphyrin since it has a particular affinity for lipoproteins. Additional components including monoclonal antibodies, receptor ligands and cytotoxins can be combined with photosensitizing agents to enhance selectivity to lens tissue and efficacy of photodegradation. Although tryptophan is the least common amino acid of human proteins it is the most photolabile of amino acids and present in high concentrations in human lens tissue.

Porphyrin-type photosensitizers used in photodynamic therapy, either used singly or in conjunction with a hydrophilic polymer, can be administered into the intralenticular space to enhance degradation of lens tissue (phacophotolysis). The photosensitive agents and their various formulations are generally known in the art.

Modern lasers are capable of producing picosend (10–12 second)bursts of extremely high intensity. In a picosecond pulse the photon intensity is quite high. Photosensitive chemicals in lens tissue can be actuated by lasers of variable power and wavelength. Hence, degradation of lens tissue by phacophotolysis provides a novel and unique method of cataract removal not heretofore practiced by prior art.

A search of the prior art did not disclose any patents that read directly on the claims of the instant invention however, the following U.S. patents were considered related:

| U.S. Pat. No. | Inventor | Issue Date |
| --- | --- | --- |
| 4,078,564 | Spina | 3/1978 |
| 4,608,050 | Wright | 8/1986 |
| 4,919,151 | Grubbs, et al | 4/1990 |
| 5,022,413 | Spina, Jr. et al | 6/1991 |
| 5,095,030 | Levy, et al | 3/1992 |
| 5,957,914 | Cook, et al | 9/1999 |

The U.S. Pat. No. 4,078,564 issued to Spina discloses an enzymatic intralenticular cataract treatment for removal of nuclear cortical and subcapsular regions of the cataractous lens through enzymatic digestion thereof The treatment comprises introduction of a concentrated solution of mixed exogenous enzymes into the nuclear and cortical regions of a cataractous lens, and after enzymatic digestion removing the liquefied cataractous material. The procedure allows removal of the nuclear, cortical and subcapsular portions of a cataractous lens through a very tiny incision in the eye and lens capsule, leaving all other structures within the eye intact.

The U.S. Pat. No. 4,608,050 issued to Wright discloses a method of treating defective lenses in the eye, wherein the natural lens is removed leaving the lens capsule intact. A curable liquid composition comprising a crosslinkable siloxane polymer, a crosslinker and a crosslinking catalyst is injected into the lens capsule where the composition cures at body temperature to a solid, transparent synthetic lens which remains clear in the presence of physiological fluids.

The U.S. Pat. No. 4,919,151 issued to Grubbs, et al discloses a synthetic polymer for endocapsular lens replacement in an eye. The polymer, which is injected into the lens capsule after removal of the lens, comprises an oxygen-stabilized photosensitive prepolymer. An example of such a prepolymer comprises polyether with urethane linkages with one or both ends capped with a functional group containing at least one double bond, such as an acrylate, a methacrylate, or a styrene. The polymerization reaction is initiated with a photoinitiator such as dimethoxyphenylacetophenone and is quenched in the presence of oxygen. Contrary to the prior art polymers, the time of curing is approximately one minute. The viscosity and thickness of the polymer formed may be tailored to achieve a desired index of refraction of between about 1.3 and 1.6.

The U.S. Pat. No. 5,022,413 issued to Spina, Jr. et al discloses a method for treating cataracts by introducing a lenticular tissue dispersing agent into the opacified lens through a small opening in the lens capsule so that the capsule remains substantially intact. The tissue dispersing agent is contained in the lens by a gel-forming substance which functions to block the opening in the lens capsule, preventing its escape. This treatment is preferably carried out in conjunction with laser induced phacofracture.

The U.S. Pat. No. 5,095,030 issued to Levy, et al discloses a group of hydro-monobenzoporphyrins "green porphyrins" (Gp) having absorption maxima in the range of 670–780 nanometers, which are useful in treating disorders or conditions which are subject to hematoporphyrin derivative (HPD) treatment in the presence of light, or in treating virus, cells and tissues generally to destroy unwanted targets. The use of the Gp permits the irradiation to use wavelengths other than those absorbed by blood. The Gp may also be conjugated to ligands specific for receptor or to specific immunoglobulins or fragments thereof to target specific tissues or cells for the radiation treatment. Use of these materials permits lower levels of drug to be used, thus preventing side reactions which might destroy normal tissues.

The U.S. Pat. No. 5,957,914 issued to Cook, et al discloses a laser photo-optic breakdown probe and handpiece system especially suited for small-incision cataract removal including an optical fiber through which a pulsed source of laser energy is delivered to a target spaced from the distal end of the fiber. The fiber is routed through a first guide tube with the target mounted at an angle on the end thereof. Holes are provided in the guide tube for the flow of infusion fluid therethrough. A second aspiration tube surrounds and provides rigidity to the guide tube, shields the distal end of the fiber and target, and serves as a channel for aspirated fluids and dislodged cataractous material. The guide tube is affixed to a transfer housing to which infusion and aspiration connections are made. The aspiration tube forms part of a handle assembly which is detachably coupled to the transfer housing.

For background purposes and as indicative of the art to which the invention relates, reference may be made to the following remaining patents found in the search:

| U.S. Pat. No. | Inventor | Issue Date |
|---|---|---|
| 4,135,516 | Spina | 1/1979 |
| 4,192,685 | Horike et al. | 3/1980 |
| 4,388,483 | Finkelmann et al. | 6/1983 |
| 4,395,806 | Wonder et al | 8/1983 |
| 4,440,570 | Kreuzer et al. | 10/1983 |
| 4,573,998 | Mazzocco | 3/1986 |
| 4,846,172 | Berlin | 7/1989 |
| 4,880,512 | Cornelius et al. | 11/1989 |
| 5,257,970 | Dougherty | 11/1993 |
| 5,298,018 | Narsisco Jr. | 3/1994 |
| 5,313,320 | Kornfield et al. | 5/1994 |
| 5,469,867 | Schmidtt | 11/1995 |
| 5,476,514 | Cumming | 12/1995 |
| 5,514,669 | Selman | 5/1996 |
| 5,705,518 | Richter et al. | 1/1998 |
| 5,738,667 | Colvard et al. | 4/1998 |
| 5,742,926 | Strong et al. | 5/1998 |
| 5,756,541 | Strong et al | 5/1998 |
| 5,829,448 | Fisher et al. | 11/1998 |
| 5,885,243 | Capetan et al. | 3/1999 |
| 5,910,510 | Strong et al. | 6/1999 |
| 5,922,821 | LeBoeuf et al. | 7/1999 |
| 5,976,175 | Hirano et al. | 11/1999 |
| 6,027,524 | Petit | 2/2000 |
| 6,074,358 | Andrew et al | 6/2000 |

Non-Patent Documents:

Borkman, R. F. et al. "The Rates of Photodestruction of Tryptophan Residues in Human and Bovine Ocular Lens Proteins", Exp Eye Res., 32:747–754, (1981).

Borkman, R. F. et al. "Fluorescence Lifetimes of Chromophores in Intact Human Lenses and Lens Proteins" Exp Eye Res., 32:313–322, (1980).

Overberger, C. G., et al., "The Preparation and Polymerization of rho-Alkylstyrenes. Effect of Structure on the Transition Temperatures of the Polymers," J. Am Chem. Soc., 75:3326–3330 (1953).

DISCLOSURE OF THE INVENTION

In the present invention, cataractous lens tissue, is liquefied by photoactive chemicals injected into the lens substance. Radiation is applied to specific regions of interest within the lens substance. The zone of lens tissue liquefaction is limited to an area which generally corresponds in size and diameter to applied laser beam radiation. Transparent fluid injected between the lens substance and capsule (hydrodissection) can protect the lens capsule from photolytic injury. As liquefaction proceeds the lens is microfractured, thus enhancing penetration of photolytic chemical available for further liquefaction. Liquefied lens tissue results in an emulsion of fluid and small fragments which may be aspirated through a tube having a diameter of about 750 microns or less. Irrigating fluid introduced within the lens capsule serves to maintain the intracapsular volume, prevent collapse of the capsular balloon,and to wash out residual cataractous lens material.

To accomplish liquefaction of lens tissue, a predetermined aliquot of photoreactive chemical is injected into the lens tissue. The chemical is administered by means of a syringe with needle that penetrates the lens capsule and engages lens tissue within the capsular balloon. Air or polymeric material delivered during the terminal phase of injection seals the lens capsule and prevents escape of phacolytic agents.

Irradiation of lens tissue containing the photosensitizing agent can be achieved by delivering light energy from an external source. The cataractous tissue is irradiated at the wavelength absorbed by the selected photoreactive agent. The present invention, therefore, represents a unique method of cataract removal by indirect photoablation.

A dual cannula surgical instrument of the present invention is employed to perform the above-discussed cataract removal. The instrument comprises a dual needle which delivers pliotoreactive chemicals into cataractous lens tissue and also removes degraded lens tissue remnants. The instrument additionally provides a conduit for the introduction of enzymes to aid in the penetration of photoreactive chemicals within the lens tissue. Aspiration of photolyzed lens tissue is accompanied by irrigation to sufficiently replace evacuated tissue. Aspiration in conjunction with irrigation serves to maintain the shape and integrity of the lens capsule during the surgical procedure.

Radiation is achieved through a light delivery means contained within the present invention The central needle serves as a guide for a fiberoptic which transmits laser radiation to lens tissue in order to perform photodynamic treatment. The fiberoptic in the central needle delivers radiation from an external point source into the capsular balloon. It has been found that optimum time intervals between administration of photosensitizing agent, illumination, and withdrawal of liquefied tissue, is dependent on adequate progression of liquefaction and judgment of the practitioner. The preferred length of time of irradiation and wavelength of light is also determined by the type and amount of photosensitve composition being used. The level of irradiance administered varies between 150–900 mW/cm2. Higher irradiances have the advantage of shortening duration of treatment. The interval of time from administration of the photosensitizing agent to light treatment can vary, depending on the density of the cataract tissue and penetration of photosensitizing agent. In general, it ranges from about one to twenty-five minutes.

Absorption of light energy by the photosensitive composition causes a reaction which destroys the tissue in which the composition has accumulated. The present invention, therefore, represents a new method and apparatus for cataract removal by photodynamic therapy. Advantageously, the present apparatus and method (referred to as phacophotolysis) permits minimally invasive cataract removal. The incision size required by phacophotolysis allows for a substantially smaller incision size than that required for conventional procedures and, importantly, without the deleterious effects of energy shock waves employed by ultrasonic or laser phacoemulsification. Complications associated with ultrasonic or laser phacoemulsification include heat injury to ocular tissue, damage to corneal endothelium, and rupture of the posterior capsule.

Following removal of decomposed cataractous tissue, a polymer matrix selected from a group consist of acrylate, methacrylate, silicone, styrene, thermopolymer, plastic polymer, photosensitive resin, organopolysiloxane, or organopolymer is then introduced into the body of the lens capsule to reconstitute the intralenticular space and serve as a refracting niedium. Additionally, an ultraviolet absorbing compound as discussed in U.S. Pat. No. 4,304,895 and U.S. Pat. No. 4,528,311 may be incorporated in the polymer matrix.

Modification of lens power by application of external laser energy is performed on lens replacement compositions that include photocurable polymers. The preferred photocurable polymers are derived from cyclic organohydrogenpolysiloxanes. Grubbs, et al (U.S. Pat. No. 4,919,151) teach that the time of curing of related synthetic polymers is about one minute at body temperature. Synthetic lens material of the type described herein are non-toxic and cures at body temperature of about 37 degrees Celsius. Polymerization and curing of the synthetic materials described herein are initiated by light using a photoinitiator such as dimethoxyphenylacetophenone,and further enhanced in the presence of an acid catalyst.

When using a biocompatible, non-immunogenic thermopolymer in a flowable, heated state, the transferred material is permitted to cool and conform to the internal shape of the capsular balloon. An intact capsule containing a flexible material restores the potential for lenticular accommodation and thus, the capability for focusing at various focal distances.

The substitute lens material can also be transferred into an expandable intralenticular balloon constructed of a resilient material selected from a group consisting of hydroxymethylmethacrylate, polymethylmethacrylate, polyethelene, polystyrene, polypropylene, polytetrafluorethylene, polybutylene terephthalate, polyether glycol, ethyl-vinyl-acetate, or it may be constructed of silicone. When inflated with substitute lens material, the inflatable balloon expands to conform to the intralenticular space. Detachable balloons are well known in the art and more fully described in U.S. Pat. No. 4,395,806 (Wonder et al). After the method has been completed, the delivery instrument is removed from the eye. The polymer material remaining within the lens capsule or intralenticular balloon is treated by an external source of radiation, such as an ultraviolet laser, to alter the refractive state of the eye.

These and other novel advantages of the present invention will become apparent from the subsequent detailed description of the preferred embodiment and the appended claims taken in conjunction with the accompanying drawings.

BEST MODE FOR CARRYING OUT THE INVENTION

Figure 1:
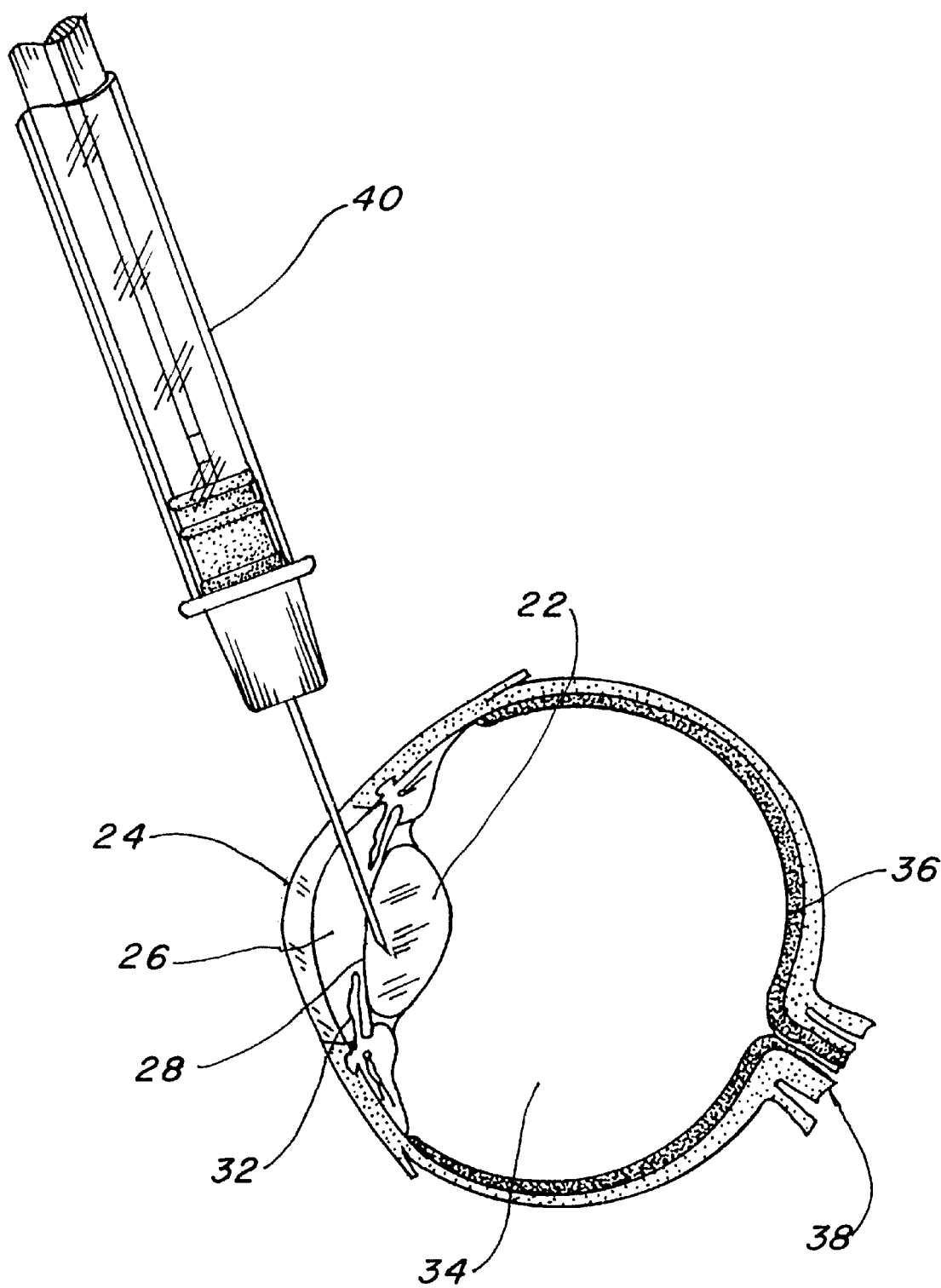
FIG. 1 is a cross sectional view of a human eye with a hypodermic syringe injecting the therapeutic photosensitive agent into the lens tissue of the eye in the preferred embodiment.
Figure 2:
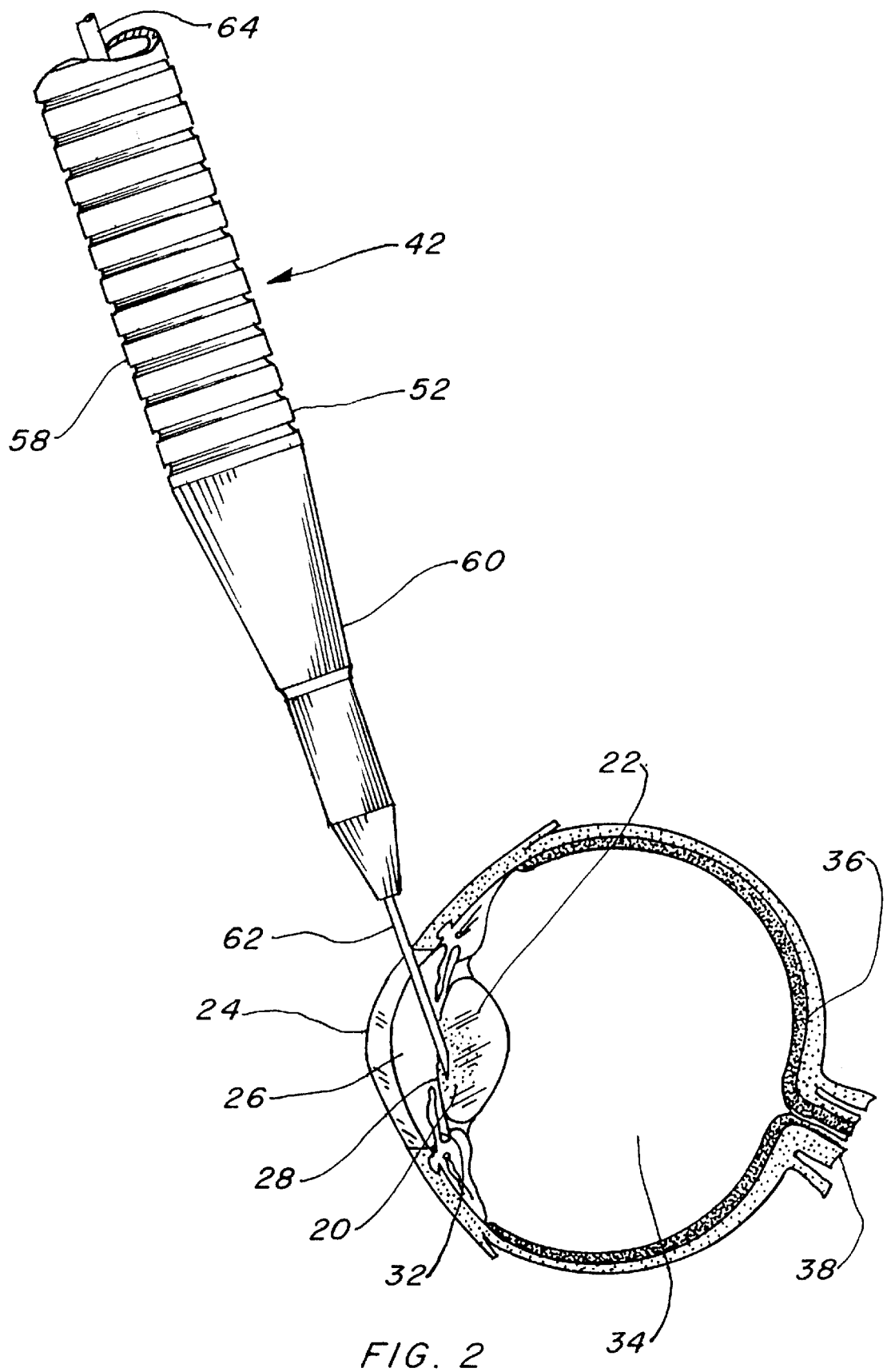
FIG. 2 is a cross sectional view of a human eye with the dual cannula surgical instrument removing the liquefied lens tissue that has been treated with a therapeutic photosensitive agent in the preferred embodiment.

The best mode for carrying out the invention is presented in terms of a process for removing cataractous lens tissue and substitution with a lens replacement material utilizing a surgical instrument in the preferred embodiment. This preferred embodiment of the process and apparatus is shown in FIGS. 1 through 12. The process is comprised of the steps of injecting a therapeutic photosensitive agent 20 into the cataractous lens tissue 22 of a human or animal eye. For clarification the cross sectional drawings in FIGS. 1–6 illustrate a human eye including the cornea 24, aqueous humor 26, lens capsule 28, intralenticular tissue or lens tissue 22, iris 32, vitreous 34, retina 36 and optic nerve 38. The injection may be by means well known in the art by medical practitioners such as a hypodermic syringe 40, as shown in FIG. 1 or the apparatus specifically developed to accomplish all of the tasks of the procedure as depicted in FIGS. 2, 3, 5 and 6. This apparatus is a dual cannula surgical instrument 42 which will be described in detail later in this specification.

The photosensitive agent 20 is composed of a substance that has the propensity to destroy ocular lens tissue and may be comprised of at least one component selected from the group consisting of chlorins, merocyanine, porphyrins, pheophorbides, purpurins, iminium salts, phthalocyanines, porphycenes, psoralen and verdins. The photosensitive agent 20 may also be a green porphyrin liposomal-preparation, complexed with low-density lipoprotein, a polypyrrolic macrocycle or chemically bound to an agent specifically reactive to lens tissue. The photosensitive agent 20 may be combined with dissimilar agents such as one selected from the group consisting of protease, lipase and carbohydrase to enhance phacolysis.

Further the photosensitive agent 20 may be confined to a intracapsular space by occlusion of the lens capsule injection site with a non-toxic polymer such as carageenan, collagen, hyaluronic acid, pectin, or xanthan gum.

The next step in the process is allowing a predetermined amount of time to elapse after injection of the photosensitive agent 20. The lapsed time is dependent upon the cataractous lens tissue 22 density and amount of penetration of the therapeutic photosensitive agent 20.

Figure 3:
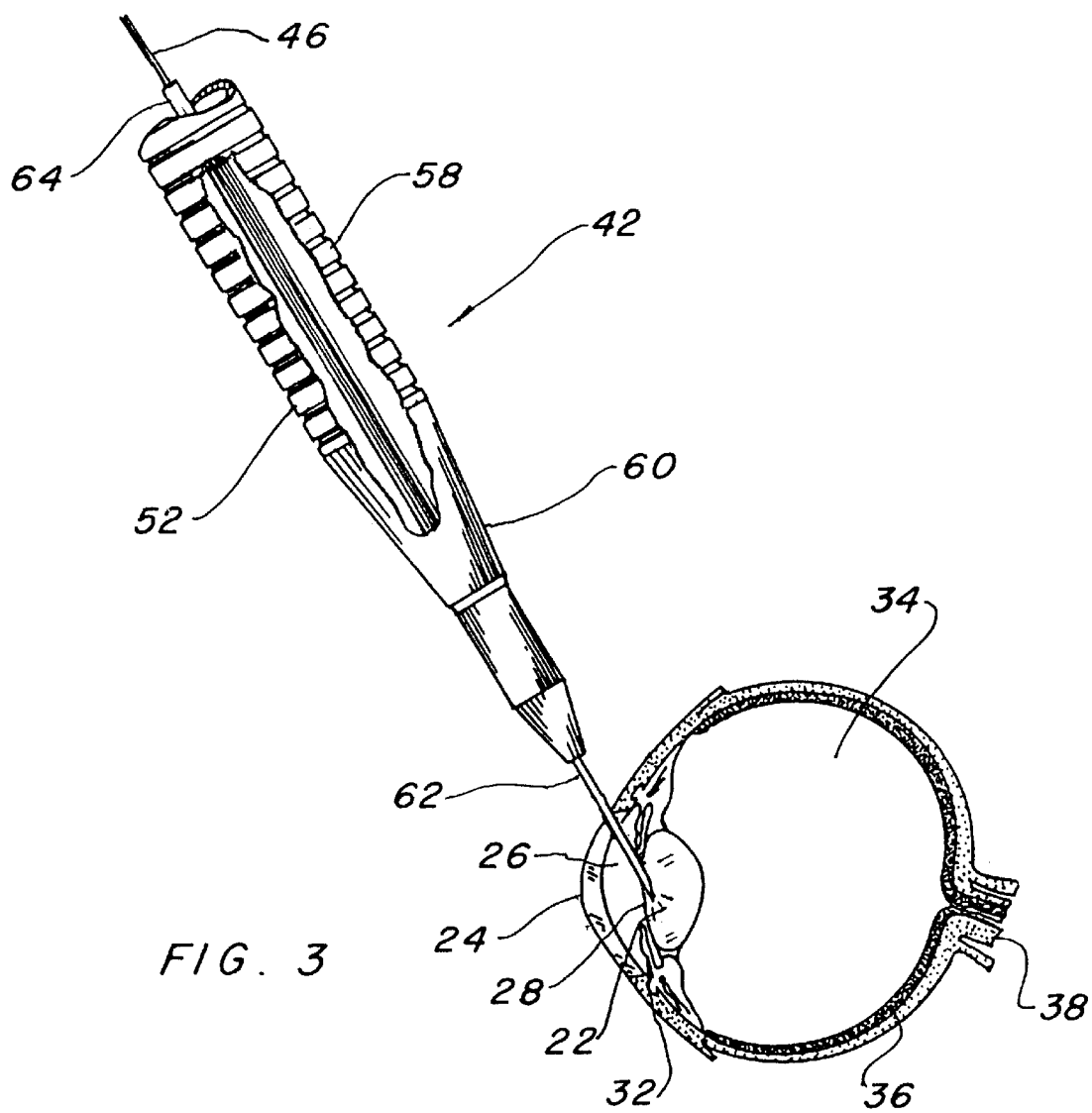
FIG. 3 is a cross sectional view of a human eye with optical fiber flexible strand disposed within the dual cannula surgical instrument radially diffusing light to the area treated with a therapeutic photosensitive agent.
Figure 4:
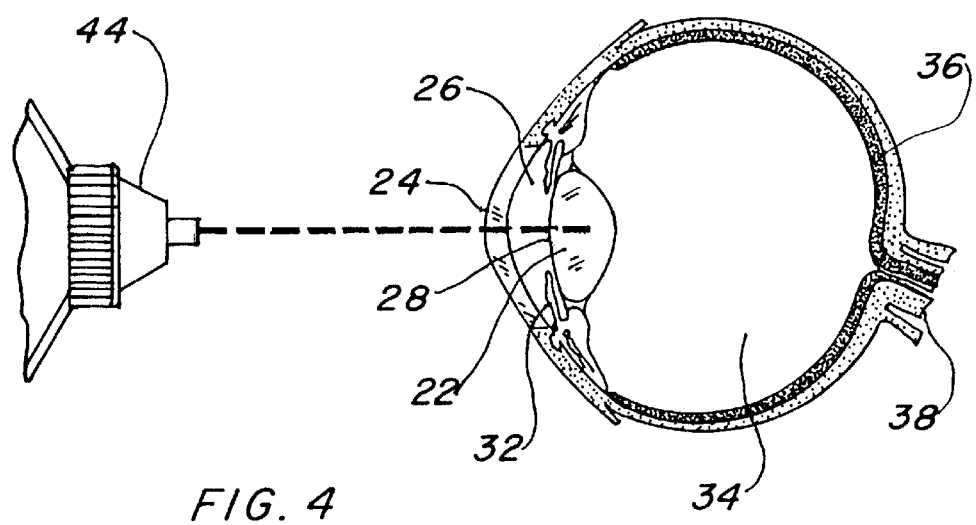
FIG. 4 is a cross sectional view of a human eye with the source of light energy in the form of a laser beam impinging on the lens tissue that has been treated with a therapeutic photosensitive agent.
Figure 5:
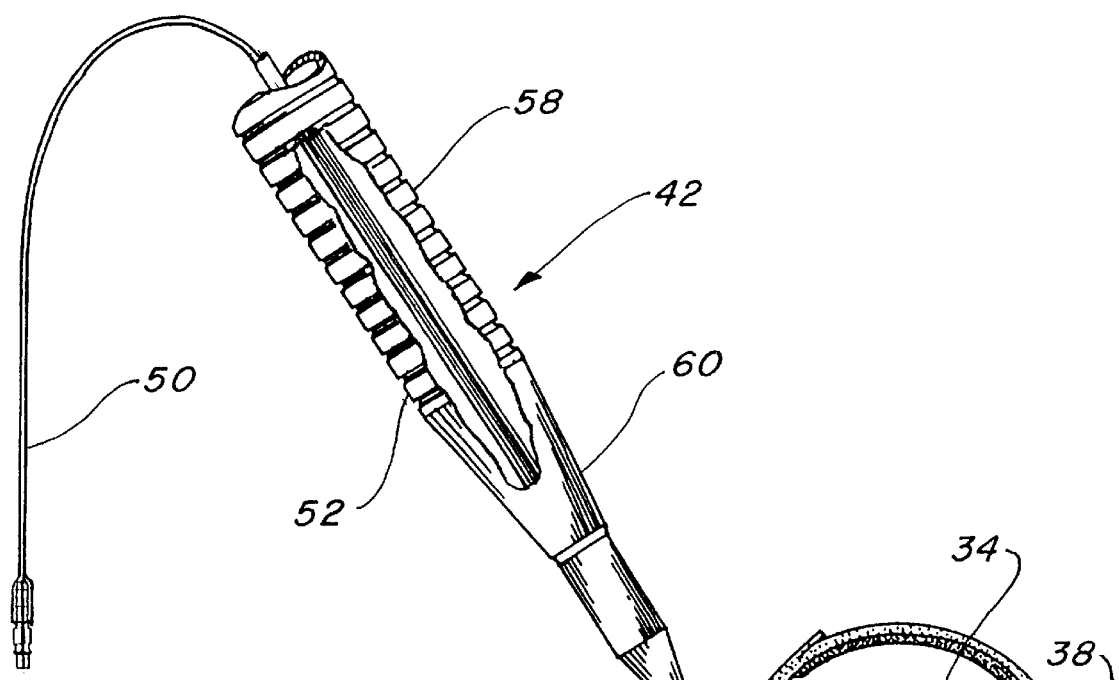
FIG. 5 is a cross sectional view of a human eye having the dual cannula surgical instrument engaging the lens tissue with a balloon partially inserted into the inner hollow needle
Figure 6:
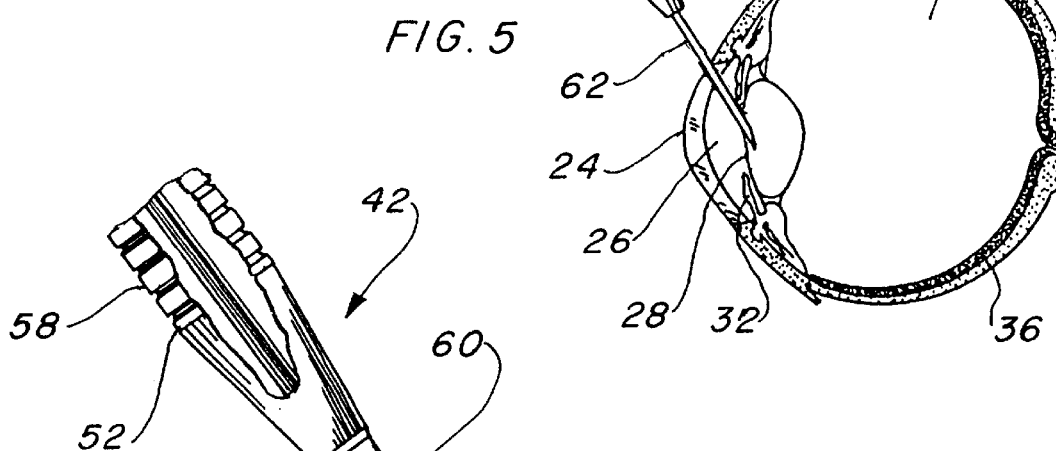
FIG. 6 is a cross sectional view of a human eye having the dual cannula surgical instrument engaging the lens tissue with a balloon inserted into the inner hollow needle and partially inflated with lens replacement material.
Figure 7:
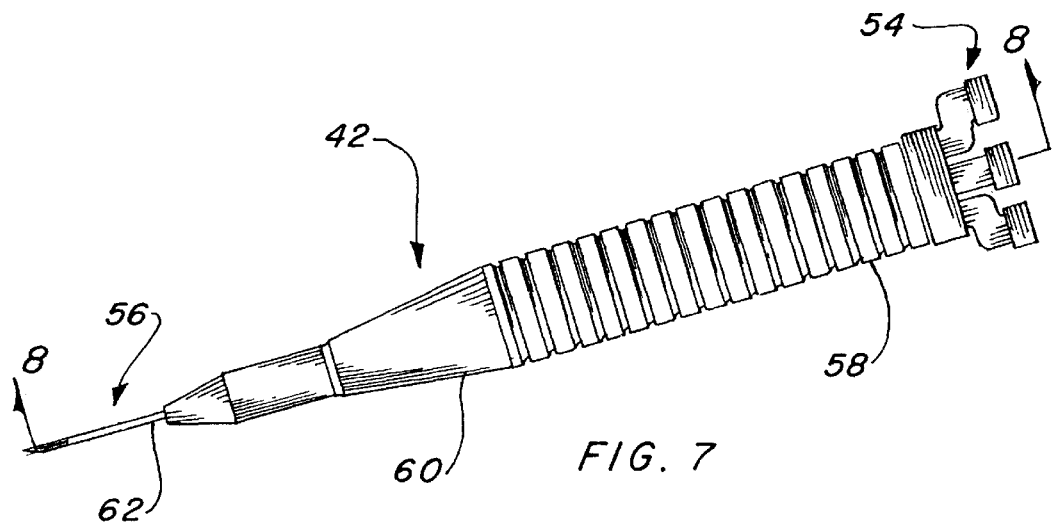
FIG. 7 is a partial isometric view of the dual cannula surgical instrument in its preferred embodiment.
Figure 8:
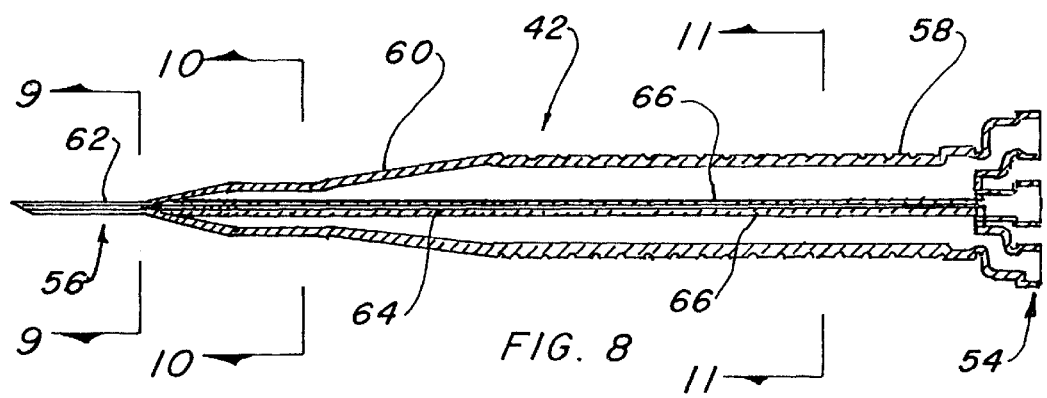
FIG. 8 is a cross sectional view of the dual cannula surgical instrument taken along lines 8—8 of FIG. 7.
Figures 9, 10, 11, 12:
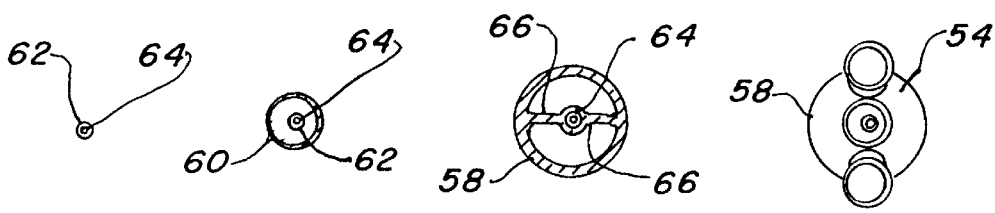
FIG. 9 is a cross sectional view of the dual cannula surgical instrument taken along lines 9—9 of FIG. 8.
FIG. 10 is a cross sectional view of the dual cannula surgical instrument taken along lines 10—10 of FIG. 8.
FIG. 11 is a cross sectional view of the dual cannula surgical instrument taken along lines 11—11 of FIG. 8.
FIG. 12 is a right end view of the dual cannula surgical instrument in its preferred embodiment.

The subsequent step in the process is exposing the therapeutic photosensitive agent 20 to a source of light energy 44 for a predetermined period of time and wavelength causing the lens 22 to microfracture and liquefy. The source of light energy 44 may be from a laser, a light emitting diode -or an incandescent lamp. The source of light energy 44 may be delivered indirectly to the lens as illustrated in FIG. 4 or directly by an optical fiber 46, as illustrated in FIG. 3. A single optical fiber strand 46 is removably disposed within the surgical instrument 42 and radially diffuses the light at its distal end.

The source of light 44 may be a laser, a light emitting diode or an incandescent lamp, however it is preferred that the source of light is a pulsed light of a wavelength and flux selected such that the lens tissue 22 in its ground state absorbs radiation and rises to an excited state and this state absorbs further radiation therefore rising to a higher state ultimately achieving photolysis.

Another source of light 44 is a laser having pulses essentially the same wavelength, with each laser pulse having a wavelength from 180 nm to 290 nm, a duration of less than $1 \times 10_{-5}$ seconds and a flux greater than $1 \times 10_{15}$ photons per square centimeter. Alternately each laser pulse may have a wavelength from 220 nm to 290 nm, a duration of less than from $5 \times 10_{-9}$ seconds to $1 \times 10_{-15}$ seconds and a flux greater than from $1 \times 10_5$ photons to $1 \times 10_5$ photons per square centimeter. Another laser pulse may have a wavelength from 220 nm to 280 nm, a duration of less than from $5 \times 10_{-10}$ seconds to $1 \times 10_{-12}$ seconds and a flux greater than from $1 \times 10_{17}$ photons to $1 \times 10_{18}$ photons per square centimeter.

Instead of laser pulses having the same wavelength they may have an essentially different wavelength such as at least one first pulsed light would have a wavelength and flux selected such that the lens proteins in their ground state absorbs radiation and rises to an excited state and at least one additional pulse of a wavelength and flux selected such that the lens tissue 22 in its excited state absorbs and sustains photolysis. The excited state of lens nucleic acids are selected from the singlet state and the triplet state and additional pulses may be applied during the lifetime of the excited states of the nucleic acids. The additional pulse may be a discrete second pulse applied within one microsecond after each first pulse is applied or simultaneously applied. Alternatively the first and second pulse may be applied in alternating sequences of more than one pulse each or the first and second pulse may be applied in alternating sequences of one pulse each.

The following step in the process of evacuating the liquefied lens tissue with a surgical instrument, preferably using the dual cannula surgical instrument 42 as illustrated in FIGS. 7–12. However, the process may use a conventional phacoemulsification and aspiration instrument in this particular step.

The final step in the process is injecting lens replacement material 48 within the human's or animal's lens capsule 28 through the surgical instrument 42 to reconstitute the lens tissue intralenticular space and serve as a refracting medium. The lens replacement material 48 forms a lens in situ which is optically clear and chemically stable in the presence of bodily fluids. The lens replacement material may be an elastomer, a photosensitive resin, a non-immunogenic and biocompatable thermoplastic, a synthetic polymer or a polymer having at least one additive such as a curing catalyst. An essential characteristic of the replacement material 48 is that is should be non-flowable at temperatures below 39 degrees C. and flowable at temperatures not higher than 45 degrees C. Further the lens replacement material 48 may be also be selected from a group consisting of, acrylate, methacrylate, silicone, styrene, thermopolymer, photosensitive resin, plastic polymer, cyclohexane, organopolymer, and organopolysiloxane.

Optionally an additional step may be added, if desired, consisting of inserting a balloon 50 into the lens capsule 28 prior to injecting lens replacement material 48 and then injecting lens replacement material into the balloon 50, instead of directly into the lens capsule 28, for reconstituting the lens tissue and to serve as a refracting medium. The balloon may be made of hydroxymethylmethacrylate, polymethylmethacrylate, polyethelene, polystyrene, polypropylene, polytetrafluorethylene, polybutylene teraphthalate, polyether glycol, ethyl-vinyl-acetate, or silicone.

The dual cannula surgical instrument 42 is illustrated in FIGS. 7–12 and is used for introducing the therapeutic photosensitive agent 20, into human or animal cataractous lens tissue 22, evacuating decomposed lens tissue while simultaneously maintaining intralenticular pressure and introducing the lens replacement material 48 within the lens capsule 28. Further utility is to insert a fiber optic strand into the lens 22 and also serves as a conduit for directing an inflatable balloon 50 into the lens capsule 28.

The surgical instrument 42 consists of a hollow cylindrical body 52 having a first end 54 and a second end 56. The body 52 has a parallel shank 58 and tapered section 60 on the second end 56 with a outer hollow needle 62 attached to the tapered section of the second end. An inner hollow needle 64 is axially disposed within the body 52 and through the outer needle 62 terminating at the body's second end 56 and is used for introducing fluids and tubular items into the lens capsule 28. The body second end 56 is in removable communication with aspiration an infusion apparatus for withdrawing decomposed cataractous lens tissue under negative pressure and supplying irrigation fluids. An internal divider 66 is disposed within the body 52 contiguous with the body parallel shank 58 and tapered section 60 and also the inner hollow needle 64 permitting dual function of the instrument simultaneously including infusion and aspiration functions of fluid materials.

The dual cannula surgical instrument 42 also serves as a conduit for a fiber optical strand 46 that is removably disposed within the inner hollow needle 64 for conducting light energy to the cataractous lens tissue 22.

Liquefaction of lens tissue can be enhanced by means of combining phacolytic chemicals with a conveyer fluid, heated to temperatures ranging from 10 degrees to 220 degrees Farenheit. Preferred conveyer fluids include balanced salt solution (BSS) and saline. However, a variety of conveyer fluids which are non-toxic and compatible with intraocular tissue can be utilized.

While the invention has been described in complete detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

What is claimed is:

1. A process for removing cataractous lens tissue and substitution thereof with a lens replacement material utilizing a surgical instrument which comprises the steps of
   a) injecting a therapeutic photosensitive agent into the cataractous lens tissue of a human or animal eye,
   b) allowing a predetermined amount of time to elapse, dependent upon cataractous lens tissue density and amount of penetration of the therapeutic photosensitive agent,
   c) exposing the therapeutic photosensitive substance to a source of light energy for a predetermined period of time and wavelength causing the lens to microfracture and liquefy,
   d) evacuating the liquefied lens tissue with a surgical instrument, and
   e) injecting lens replacement material within the human's or animal's lens capsule through said surgical instrument to reconstitute the lens tissue intralenticular space and serve as a refracting medium.

2. The process for removing cataractous lens tissue and substitution thereof with a lens replacement material as recited in claim 1 wherein said photosensitive agent is composed of a substance that has the propensity to destroy ocular lens tissue.

3. The process for removing cataractous lens tissue and substitution thereof with a lens replacement material as recited in claim 1 wherein said photosensitive agent further comprises at least one component selected from the group consisting of chlorins, merocyanine, porphyrins, pheophorbides, purpurins, iminium salts, phthalocyanines, porphycenes, psoralen and verdins.

4. The process for removing cataractous lens tissue and substitution thereof with a lens replacement material as recited in claim 1 wherein said photosensitive agent further comprises a green porphyrin liposomal preparation.

5. The process for removing cataractous lens tissue and substitution thereof with a lens replacement material as recited in claim 1 wherein said photosensitive agent is complexed with low-density lipoprotein.

6. The process for removing cataractous lens tissue and substitution thereof with a lens replacement material as recited in claim 1 wherein said photosensitive agent further comprises a polypyrrolic macrocycle.

7. The process for removing cataractous lens tissue and substitution thereof with a lens replacement material as recited in claim 1 wherein said photosensitive agent is chemically bound to an agent specifically reactive to lens tissue.

8. The process for removing cataractous lens tissue and substitution thereof with a lens replacement material as recited in claim 1 wherein said source of light is selected from the group consisting of a laser, a light emitting diode and an incandescent lamp.

9. The process for removing cataractous lens tissue and substitution thereof with a lens replacement material as recited in claim 1 wherein said source of light is a pulsed light of a wavelength and flux selected such that the lens in its ground state absorbs radiation and rises to an excited state and this state absorbs further radiation therefore rising to a higher state ultimately achieving photolysis.

10. The process for removing cataractous lens tissue and substitution thereof with a lens replacement material as recited in claim 1 wherein said source of light energy is delivered to the lens by an optical fiber within the surgical instrument which radially diffuses the light.

11. The process for removing cataractous lens tissue and substitution thereof with a lens replacement material as recited in claim 1 wherein said lens replacement material further comprises an elastomer.

12. The process for removing cataractous lens tissue and substitution thereof with a lens replacement material as recited in claim 1 wherein said lens replacement material further comprises a photosensitive resin.

13. The process for removing cataractous lens tissue and substitution thereof with a lens replacement material as recited in claim 1 wherein said lens replacement material further comprises a non-immunogenic and biocompatable thermoplastic.

14. The process for removing cataractous lens tissue and substitution thereof with a lens replacement material as recited in claim 1 wherein said lens replacement material is non-flowable at temperatures below 39 degrees C. and flowable at temperatures not higher than 45 degrees C.

15. The process for removing cataractous lens tissue and substitution thereof with a lens replacement material as recited in claim 1 wherein said lens replacement material further comprises a synthetic polymer.

16. The process for removing cataractous lens tissue and substitution thereof with a lens replacement material as recited in claim 1 wherein said lens replacement material is selected from the group consisting acrylate, polymethylmethacrylate, methacrylate, silicone, styrene, thermopolymer, photosensitive resin, plastic polymer, cyclohexane, organopolymer, or organopolysiloxane.

17. The process for removing cataractous lens tissue and substitution thereof with a lens replacement material as recited in claim 1 wherein said lens replacement material forms a lens in situ which is optically clear and chemically stable in the presence of bodily fluids.

18. The process for removing cataractous lens tissue and substitution thereof with a lens replacement material as recited in claim 1 wherein said liquefaction of lens tissue can be enhanced by means of combining phacolytic chemicals with a conveyer fluid, heated to temperature ranging from 10 degrees to 220 degrees Farenheit.

19. The process for removing cataractous lens tissue and substitution thereof with a lens replacement material as recited in claim 1 wherein said photosensitive agent further comprises a combination of dissimilar agents.

20. The process for removing cataractous lens tissue and substitution thereof with a lens replacement material as recited in claim 19 wherein said combination of dissimilar agents is selected from the group consisting of protease, lipase and carbohydrase.

21. The process for removing cataractous lens tissue and substitution thereof with a lens replacement material as recited in claim 1 wherein said photosensitive agent is confined to the intracapsular space by occlusion of the lens capsule injection site with a non-toxic polymer.

22. The process for removing cataractous lens tissue and substitution thereof with a lens replacement material as recited in claim 21 wherein said non-toxic polymer is selected from the group consisting of carageenan, collagen, hyaluronic acid, pectin, and xanthan gum.

23. The process for removing cataractous lens tissue and substitution thereof with a lens replacement material as recited in claim 1 wherein said source of light is comprised of laser pulses having essentially the same wavelength.

24. The process for removing cataractous lens tissue and substitution thereof with a lens replacement material as recited in claim 23 wherein each laser pulse has a wavelength within the range of 180 to 290 nm, a duration less than $1\times10^{-5}$ seconds and a flux greater than $1\times10^{15}$ photons per square centimeter.

25. The process for removing cataractous lens tissue and substitution thereof with a lens replacement material as recited in claim 23 wherein each laser pulse has a wavelength from 220 nm to 290 nm, a duration of less than from $5\times10^{-9}$ seconds to $1\times10^{-31.5}$ seconds and a flux greater than from $1\times10^5$ photons to $1\times10^{18}$ photons per square centimeter.

26. The process for removing cataractous lens tissue and substitution thereof with a lens replacement material as recited in claim 23 wherein each laser pulse has a wavelength from 220 nm to 280 nm, a duration of less than from $5\times10^{-10}$ seconds to $1\times10^{-12}$ seconds and a flux greater than from $1\times10^{17}$ photons to $1\times10^{18}$ photons per square centimeter.

27. The process for removing cataractous lens tissue and substitution thereof with a lens replacement material as recited in claim 1 wherein said pulsed light is comprised of laser pulses having essentially a different wavelength.

28. The process for removing cataractous lens tissue and substitution thereof with a lens replacement material as recited in claim 27 wherein said source of light further comprises at least one first pulsed light of a wavelength and flux selected such that the lens proteins in their ground state absorbs radiation and rises to an excited state and at least one additional pulse of a wavelength and flux selected such that said lens in their excited state absorb and undergo photolysis.

29. The process for removing cataractous lens tissue and substitution thereof with a lens replacement material as recited in claim 28 wherein a second pulse is applied within one microsecond after each first pulse is applied.

30. The process for removing cataractous lens tissue and substitution thereof with a lens replacement material as recited in claim 28 wherein said additional pulse is simultaneously applied.

31. The process for removing cataractous lens tissue and substitution thereof with a lens replacement material as recited in claim 28 wherein said first and second pulse are applied in alternating sequences of more than one pulse each.

32. The process for removing cataractous lens tissue and substitution thereof with a lens replacement material as recited in claim 28 wherein said first and second pulse are, applied in alternating sequences of one pulse each.

33. The process for removing cataractous lens tissue and substitution thereof with a lens replacement material as recited in claim 1 wherein said lens replacement material further comprises a polymer having at least one additive.

34. The process for removing cataractous lens tissue and substitution thereof with a lens replacement material as recited in claim 33 wherein said additive is a curing catalyst.

35. The process for removing cataractous lens tissue and substitution thereof with a lens replacement material as recited in claim 1 further comprising an additional step of inserting a balloon into the intralenticular space of a human or animal eye prior to injecting lens replacement material and injecting lens replacement material into the balloon to reconstitute the lens and serve as a refracting medium.

36. The process for removing cataractous lens tissue and substitution thereof with a lens replacement material as recited in claim 35 wherein said balloon is made of a substance selected from the group consisting of hydroxymethylmethacrylate, polymethylmethacrylate, polyethelene, polystyrene, polypropylene, polytetrafluorethylene, polybutylene teraphthalate, polyether glycol, ethyl-vinyl-acetate, and silicone.

37. A process for removing cataractous lens tissue and substitution with a lens replacement material in a human or animal which comprises the steps of:
   a) injecting into the cataractous lens tissue an effective amount of therapeutic photosensitive agent,
   b) exposing the therapeutic photosensitive substance to a source of light energy causing the lens to liquefy,
   c) evacuating the liquefied lens tissue with a surgical instrument, and
   d) injecting lens replacement material within the intralenticular space of a human or animal eye to reconstitute the lens and serve as a refracting medium.

38. A dual cannula surgical instrument for introducing a therapeutic photosensitive agent into lens tissue of a human or animal eye, evacuating decomposed lens tissue while simultaneously maintaining intralenticular pressure and introducing a lens replacement material comprising:
   a) a hollow cylindrical body having a first end and a second end,
   b) said body having a parallel shank and a tapered section on the second end,
   c) an outer hollow needle is attached to the tapered section of the second end,
   d) an inner hollow needle axially disposed within the body and outer needle, said inner needle terminating at the body's second end, for introducing fluids and tubular items into the lens capsule,
   e) said body second end in communication with an aspiration and infusion apparatus for withdrawing decomposed cataractous lens tissue under negative pressure and injection of a therapeutic photosensitive agent and a lens replacement material, and,
   f) an internal divider disposed within the body contiguous with both the body and the inner hollow needle permitting dual function of the instrument simultaneously including infusion and aspiration functions of fluid materials.

39. The dual cannula surgical instrument as recited in claim 38 further comprising a fiber optical strand removably disposed within the inner hollow needle for conducting light energy to the cataractous lens tissue.

* * * * *